United States Patent
Fan et al.

(10) Patent No.: US 12,369,904 B2
(45) Date of Patent: Jul. 29, 2025

(54) SURGICAL CONDUIT ANASTOMOSIS SUTURE TENSIONING DEVICE

(71) Applicant: Ning Fan, Qingdao (CN)

(72) Inventors: Ning Fan, Qingdao (CN); Chao Yang, Qingdao (CN); Jinzhen Cai, Qingdao (CN); Yuan Guo, Qingdao (CN); Qingguo Xu, Qingdao (CN); Chuanshen Xu, Qingdao (CN); Jianhong Wang, Qingdao (CN); Yandong Sun, Qingdao (CN); Feng Wang, Qingdao (CN); Bin Zhang, Qingdao (CN)

(73) Assignee: Ning Fan, Qingdao (CN)

( * ) Notice: Subject to any disclaimer, the term of this patent is extended or adjusted under 35 U.S.C. 154(b) by 405 days.

(21) Appl. No.: 17/809,552

(22) Filed: Jun. 28, 2022

(65) Prior Publication Data

US 2023/0255619 A1    Aug. 17, 2023

(30) Foreign Application Priority Data

Feb. 15, 2022  (CN) .................. 202210136496.X

(51) Int. Cl.
 *A61B 17/04* (2006.01)
 *A61B 17/11* (2006.01)

(52) U.S. Cl.
 CPC .......... *A61B 17/0469* (2013.01); *A61B 17/11* (2013.01)

(58) Field of Classification Search
 CPC . A61B 17/0485; A61B 17/0483; A61B 17/11; A61B 17/1128; A61B 17/0469; A61B 17/04; A61B 2017/0496; A61B 2017/1107; A61B 2017/1132; A61B 2017/1135; A61B 2017/1139;
(Continued)

(56) References Cited

U.S. PATENT DOCUMENTS

| | | | | |
|---|---|---|---|---|
| 5,391,176 A | * | 2/1995 | de la Torre | ........ A61B 17/0469 606/139 |
| 2016/0193030 A1 | * | 7/2016 | Cully | ........................ A61F 2/97 623/1.12 |

* cited by examiner

*Primary Examiner* — Katherine M Shi
*Assistant Examiner* — Mohammed S Adam
(74) *Attorney, Agent, or Firm* — Au Law Office, P.C.; Yiu F. Au

(57) ABSTRACT

The invention discloses a surgical conduit anastomosis suture tensioning device, which comprises a tube A and a tube B, wherein the tube A is a preset tube, and the tube B is a suture hooking tube; the preset tube comprises a connector, a first crossbar and a first tail, the first crossbar is arranged between the connector and the first tail, the connector is vertical to the first crossbar and magnetic, and a plurality of grooves are evenly distributed on the surface of the first crossbar; the suture hooking tube comprises a suture hooking head, a second crossbar and a second tail, the second crossbar is arranged between the suture hooking head and the second tail, the suture hooking head is vertical to the second crossbar and magnetic, a suture hooking slot is arranged at the tip of the suture hooking head in a forky form, the surface of the second crossbar is smooth and free from grooves, and the second tail has the same structure as the first tail. The invention relates to the technical field of surgical suture tensioning device, in particular provides a surgical conduit anastomosis suture tensioning device, which can effectively improve the continuous conduit suture efficiency and precision, promote uniform anastomotic healing, and reduce anastomotic stenosis caused by scars.

20 Claims, 2 Drawing Sheets

(58) Field of Classification Search
CPC .... A61B 2017/0474; A61B 2017/0477; A61B 2017/0479; A61B 2017/047
See application file for complete search history.

SURGICAL CONDUIT ANASTOMOSIS SUTURE TENSIONING DEVICE

RELATED APPLICATIONS

This application claims priority to China Patent Application No. 202210136496.X, filed Feb. 15, 2022; the above-identified application is hereby incorporated by reference herein.

TECHNICAL FIELD

The invention relates to the technical field of surgical suture tensioning device, in particular to a surgical conduit anastomosis suture tensioning device.

BACKGROUND ART

The surgical operation requires high continuous conduit (including blood vessels, biliary ducts, intestinal tracts, nephric ducts, bladder wall, uterine wall, vagina, pancreas, liver section, and other organs or tissues which can be continuously sutured) anastomosis. The uniform suturing spacing helps good apposition on both sides of the sutured wall, reduces scar formation after healing, and prevents anastomotic stenosis. To ensure continuous conduit anastomosis, the suture needs to be tensioned for each stitch, often resulting in uneven suture density when suturing is completed. The solution is to tension the stitches one by one after the needle is inserted and withdrawn evenly. However, there is no device for suture tensioning to help surgeons tension the suture quickly and efficiently after a dozen stitches. The surgeons only grasp the two ends of the suture and forcibly pull them for tensioning after 2-3 stitches. Even if the polypropylene suture is used, the adverse consequence of tissue tearing, suture breakage, or loosening may be caused. At present, there is no suture tensioning device that can assist the surgeons in completing continuous anastomosis in the open and minimally invasive surgeries.

SUMMARY OF THE INVENTION

Because of the above situation, to remedy the above existing defects, the invention provides a surgical conduit anastomosis suture tensioning device, which can effectively improve the continuous conduit suture efficiency and precision, promotes the continuous conduit suture efficiency and precision uniform anastomotic healing and reduces the anastomotic stenosis caused by scars.

The invention provides the following technical proposal: a surgical conduit anastomosis suture tensioning device proposed by the invention comprises a tube A and a tube B, the tube A is a preset tube, which is placed on the pre-suturing path during suturing, and the tube B is a suture hooking tube, which is used for hooking the suture during tensioning;

The preset tube comprises a connector, a first crossbar and a first tail, the first crossbar is arranged between the connector and the first tail, the connector is vertical to the first crossbar, magnetic and is used to be placed at the suture starting point, a plurality of grooves are evenly distributed on the surface of the first crossbar, and the first tail has two shapes, in which one is a 5 mm long sector structure with a grasping hole in the middle, and the other is a 2 cm long handle structure, the sector structure is used for minimally invasive surgery, the grasping hole is convenient for grasping the grasper, and the handle structure is used for open surgery and convenient for the thumb and the index finger to hold;

The suture hooking tube comprises a suture hooking head, a second crossbar and a second tail, the second crossbar is arranged between the suture hooking head and the second tail, the suture hooking head is vertical to the second crossbar, magnetic and used for suture hooking during tensioning and can be magnetically adsorbed with the connector, a suture hooking slot is arranged at the tip of the suture hooking head in a forky form and used for suture hooking, the surface of the second crossbar is smooth and free from grooves, and the second tail has the same structure as the first tail.

Preferably, the connector is 3-5 mm long, and the first crossbar is 5-10 cm long.

Preferably, the suture hooking head has an equal length to the connector.

Preferably, the second crossbar is 3-6 cm long.

Further, the spacing between two groups of adjacent grooves on the surface of the first crossbar is 2-4 mm.

The invention has the following beneficial effects by adopting the above structure: a surgical conduit anastomosis suture tensioning device proposed by the invention greatly improves the anastomosis efficiency and precision of the conduit (including blood vessels, biliary ducts, intestinal tracts, nephric ducts, bladder wall, uterine wall, vagina, pancreas, liver section and other organs or tissues which can be can continuously sutured) suture, reduces the suture difficulty, promotes the uniform anastomotic healing, reduces anastomotic stenosis caused by scars and guarantees the continuous suture quality through the connection between the tube A (preset tube) and the tube B (suture hooking tube), ensuring the homogeneous and standardized surgical continuous suture, and effectively solving the technical problem that the continuous suture efficiency and precision is controlled by experiences as there is no suture tensioning device that can assist the surgeons in completing continuous anastomosis in the open and minimally invasive surgeries.

DESCRIPTION OF THE DRAWINGS

The drawings are provided for further understanding of the invention. They form part of the specification that are used to explain the invention together with their embodiments, and do not constitute a limitation on the invention. In the drawings.

Figure 1:
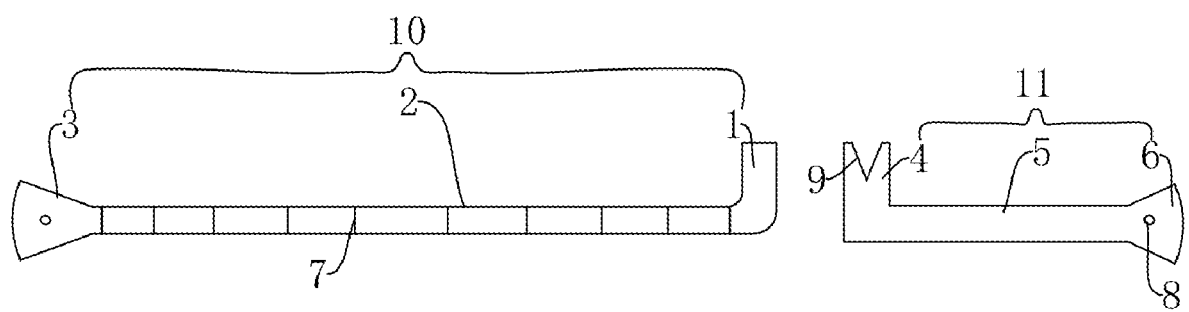
FIG. 1 is the schematic diagram for the overall structure of a surgical conduit anastomosis suture tensioning device used for minimally invasive surgery in the invention.

Wherein, 1. Connector, 2. First crossbar, 3. First tail, 4. Suture hooking head, 5. Second crossbar, 6. Second tail, 7. Groove, 8. Grasping hole, 9. Suture hooking slot, 10. Tube A, 11. Tube B.

EMBODIMENTS

The technical proposal in the embodiments of the invention is clearly and completely described below in combination with the drawings. Obviously, the described embodiments are only part of the embodiments of the invention, but not all embodiments. Based on the embodiments of the invention, all other embodiments obtained by ordinary technicians in the field without creative labor are within the scope of protection of the invention.

It should be noted that the words "front," and "rear," "left" and "right", "upper" and "lower" used in the following description refer to the directions in the drawings. The words "inside" and "outside" respectively refer to the directions towards or away from the geometric center of a particular part.

Embodiment 1

As shown in FIG. 1, the invention adopts the following technical proposal when used for minimally invasive surgery: a surgical conduit anastomosis suture tensioning device comprises a tube A 10 and a tube B 11, the tube A 10 is a preset tube, which is placed on the pre-suturing path during suturing, and the tube B 11 is a suture hooking tube, which is used for hooking the suture during tensioning; the preset tube comprises a connector 1, a first crossbar 2 and a first tail 3, the first crossbar 2 is arranged between the connector 1 and the first tail 3, the connector 1 is vertical to the first crossbar 2, 3-5 cm long and magnetic and is used to be placed at the suture starting point, a plurality of grooves 7 are evenly distributed on the surface of the first crossbar 2, the spacing between two groups of adjacent grooves 7 on the surface of the first crossbar 2 is 2-4 mm, the first crossbar 2 is 5-10 cm long, the first tail 3 is a 5 mm long sector structure with a grasping hole 8 in the middle, the sector structure is used for minimally invasive surgery, and the grasping hole 8 is convenient for grasping the grasper; the suture hooking tube comprises a suture hooking head 4, a second crossbar 5 and a second tail 6, the second crossbar 5 is arranged between the suture hooking head 4 and the second tail 6, the suture hooking head 4 is vertical to the second crossbar 5, has equal length to the connector 1, is magnetic and is used for suture hooking during tensioning, and can be magnetically adsorbed with the connector 1, a suture hooking slot 9 is arranged at the tip of the suture hooking head 4 in a forky form and used for suture hooking, the surface of the second crossbar 5 is smooth and free from grooves 7, the second crossbar 5 is 3-6 cm long, and the second tail 6 has the same structure as the first tail 3.

Embodiment 2

Figure 2:
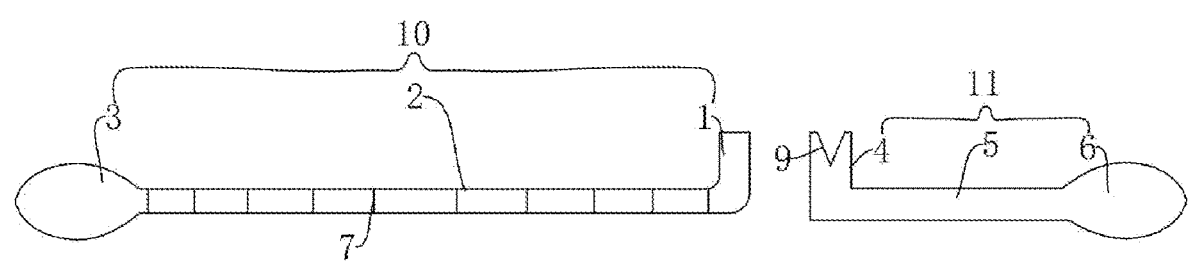
FIG. 2 is the schematic diagram for the overall structure of a surgical conduit anastomosis suture tensioning device used for open surgery in the invention.

As shown in FIG. 2, the invention adopts the following technical proposal when used for minimally invasive surgery: a surgical conduit anastomosis suture tensioning device comprises a tube A 10 and a tube B 11, the tube A 10 is a preset tube, which is placed on the pre-suturing path during suturing, and the tube B 11 is a suture hooking tube, which is used for hooking the suture during tensioning; the preset tube comprises a connector 1, a first crossbar 2 and a first tail 3, the first crossbar 2 is arranged between the connector 1 and the first tail 3, the connector 1 is vertical to the first crossbar 2, 3-5 cm long and magnetic and is used to be placed at the suture starting point, a plurality of grooves 7 are evenly distributed on the surface of the first crossbar 2, the spacing between two groups of adjacent grooves 7 on the surface of the first crossbar 2 is 2-4 mm, the first crossbar 2 is 5-10 cm long, and the first tail 3 is a 2 cm long handle structure, which is used for open surgery and convenient for the thumb and the index finger to hold; the suture hooking tube comprises a suture hooking head 4, a second crossbar 5 and a second tail 6, the second crossbar 5 is arranged between the suture hooking head 4 and the second tail 6, the suture hooking head 4 is vertical to the second crossbar 5, has an equal length to the connector 1, is magnetic and is used for suture hooking during tensioning, and can be magnetically adsorbed with the connector 1, a suture hooking slot 9 is arranged at the tip of the suture hooking head 4 in a forky form and used for suture hooking, the surface of the second crossbar 5 is smooth and free from grooves 7, the second crossbar 5 is 3-6 cm long, and the second tail 5 has the same structure as the first tail 3.

During continuous suturing, the tube A 10 is placed on the suture line for two conduits, the connector 1 faces the suture starting direction, the second stitch is fallen into the first groove 7 of the first crossbar 2 close to the connector 1 after completion of the first stitch and knotting, suturing is performed in turn in the direction of the first tail 3, each stitch is fallen into the first groove 7 of the first crossbar 2 without suture tensioning, and the suture is tensioned after the last stitch;

Suture tensioning process: after magnetically connecting the suture hooking head 4 of the tube B 11 with the connector 1, tilt the side to retreat the first stitch to the tail together, hook the suture for the first stitch by using the suture hooking slot 9 with a forky tip for the suture hooking head 4 to separate the connector 1 and the suture hooking head 4 which are connected magnetically, and send the suture for the first stitch to the most appropriate position by using the suture hooking slot 9 with a forky tip for the suture hooking head 4 while pulling up the tail suture by the connector 1. Repeat the above steps to tension the second stitch, the third stitch and so on until the last stitch. Also, ensure that the tissue on each stitch is introversive and the stitch length is even to complete the suture tensioning process precisely and effectively.

It should be noted that the relational terms such as first and second in the text are only used to distinguish one entity or operation from another entity or operation, and do not necessarily require or imply any such actual relationship or order between these entities or operations. Also, the terms "comprise" and "contain" or any other variants are intended to cover non-exclusive "contain", so that the process, method, material or device comprising a series of elements not only comprises those elements, but also other elements not listed clearly or inherent elements for the process, method, material or device.

Although the embodiments of the invention have been shown and described, it is understandable for the ordinary technicians in the field that these embodiments can be changed, modified, replaced, and varied in various ways without deviation from the principle and spirit of the invention. The attached claims and their equivalents limit the scope of the invention.

The invention claimed is:

1. A surgical conduit anastomosis suture tensioning device, wherein the surgical conduit anastomosis suture tensioning device comprises a preset tube and a suture hooking tube;

wherein the preset tube comprises a connector, a first crossbar, and a first tail, the first crossbar is arranged between the connector and the first tail, the connector is vertical to the first crossbar and magnetic, and a plurality of grooves are evenly distributed on a surface of the first crossbar;

wherein the suture hooking tube comprises a suture hooking head, a second crossbar and a second tail, the second crossbar is arranged between the suture hooking head and the second tail, the suture hooking head is vertical to the second crossbar and magnetic, a suture hooking slot is arranged at a tip of the suture hooking head in a forky form, a surface of the second crossbar is smooth and free from grooves, and the second tail has substantially the same structure as the first tail.

2. The surgical conduit anastomosis suture tensioning device of claim 1, wherein the connector is about 3-5 mm long, and the first crossbar is 5-10 cm long.

3. The surgical conduit anastomosis suture tensioning device of claim 2, wherein the suture hooking head has a substantially equal length to the connector.

4. The surgical conduit anastomosis suture tensioning device of claim 3, wherein the second crossbar is about 3-6 cm long.

5. The surgical conduit anastomosis suture tensioning device of claim 1, wherein a spacing between two groups of adjacent grooves of the plurality of grooves on the surface of the first crossbar is about 2-4 mm.

6. The surgical conduit anastomosis suture tensioning device of claim 1, wherein the first tail comprises a sector structure of 5 mm in length, and wherein a middle of the sector structure comprises a grasping hole.

7. The surgical conduit anastomosis suture tensioning device of claim 1, wherein the first tail comprises a sector structure of about 5 mm in length.

8. The surgical conduit anastomosis suture tensioning device of claim 7, wherein a middle of the sector structure comprises a grasping hole.

9. The surgical conduit anastomosis suture tensioning device of claim 1, wherein the first tail comprises a handle structure.

10. The surgical conduit anastomosis suture tensioning device of claim 9, wherein the handle structure is about 2 cm in length.

11. A surgical conduit anastomosis suture tensioning device, wherein the surgical conduit anastomosis suture tensioning device comprises a preset tube and a suture hooking tube;
wherein the preset tube comprises a connector, a first crossbar, and a first tail, the first crossbar is arranged between the connector and the first tail, the connector is vertical to the first crossbar and magnetic, a plurality of grooves are evenly distributed on a surface of the first crossbar, and the first tail comprises a 5 mm long sector structure with a grasping hole in the middle;
wherein the suture hooking tube comprises a suture hooking head, a second crossbar and a second tail, the second crossbar is arranged between the suture hooking head and the second tail, the suture hooking head is vertical to the second crossbar and magnetic, a suture hooking slot is arranged at a tip of the suture hooking head in a forky form, a surface of the second crossbar is smooth and free from grooves, and the second tail has substantially the same structure as the first tail.

12. The surgical conduit anastomosis suture tensioning device of claim 11, wherein the connector is 3-5 mm long, and the first crossbar is 5-10 cm long.

13. The surgical conduit anastomosis suture tensioning device of claim 12, wherein the suture hooking head has an equal length to the connector.

14. The surgical conduit anastomosis suture tensioning device of claim 13, wherein the second crossbar is 3-6 cm long.

15. The surgical conduit anastomosis suture tensioning device of claim 11, wherein a spacing between two groups of adjacent grooves of the plurality of grooves on the surface of the first crossbar is 2-4 mm.

16. A surgical conduit anastomosis suture tensioning device, wherein the surgical conduit anastomosis suture tensioning device comprises a preset tube and a suture hooking tube;
wherein the preset tube comprises a connector, a first crossbar, and a first tail, the first crossbar is arranged between the connector and the first tail, the connector is vertical to the first crossbar and magnetic, a plurality of grooves are evenly distributed on a surface of the first crossbar, and the first tail comprises a 2 cm long handle structure;
wherein the suture hooking tube comprises a suture hooking head, a second crossbar and a second tail, the second crossbar is arranged between the suture hooking head and the second tail, the suture hooking head is vertical to the second crossbar and magnetic, a suture hooking slot is arranged at a tip of the suture hooking head in a forky form, a surface of the second crossbar is smooth and free from grooves, and the second tail has the same structure as the first tail.

17. The surgical conduit anastomosis suture tensioning device of claim 16, wherein the connector is about 3-5 mm long, and the first crossbar is about 5-10 cm long.

18. The surgical conduit anastomosis suture tensioning device of claim 17, wherein the suture hooking head has a equal length to the connector.

19. The surgical conduit anastomosis suture tensioning device of claim 18, wherein the second crossbar is 3-6 cm long.

20. The surgical conduit anastomosis suture tensioning device of claim 16, wherein a spacing between two groups of adjacent grooves of the plurality of grooves on the surface of the first crossbar is 2-4 mm.

\* \* \* \* \*